(12) United States Patent
Fojtik

(10) Patent No.: US 10,695,041 B2
(45) Date of Patent: *Jun. 30, 2020

(54) EXPANDABLE DEVICES FOR POSITIONING ORGANS

(71) Applicant: Manual Surgical Sciences, LLC, Minneapolis, MN (US)

(72) Inventor: Shawn P. Fojtik, Park City, UT (US)

(73) Assignee: Manual Surgical Sciences LLC, Minneapolis, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/684,938

(22) Filed: Aug. 23, 2017

(65) Prior Publication Data

US 2018/0035993 A1 Feb. 8, 2018

Related U.S. Application Data

(63) Continuation-in-part of application No. 14/635,435, filed on Feb. 27, 2015.
(Continued)

(51) Int. Cl.
*A61B 17/02* (2006.01)
*A61B 90/00* (2016.01)
(Continued)

(52) U.S. Cl.
CPC .......... *A61B 17/0218* (2013.01); *A61B 90/04* (2016.02); *A61M 25/00* (2013.01); *A61M 25/0082* (2013.01); *A61B 2017/00557* (2013.01); *A61B 2017/00818* (2013.01); *A61B 2017/22071* (2013.01);
(Continued)

(58) Field of Classification Search
CPC .............. A61M 29/02; A61M 25/1002; A61M 25/1011; A61M 25/1018; A61M 2025/1047; A61M 2025/1059; A61M 2025/1072

See application file for complete search history.

(56) References Cited

U.S. PATENT DOCUMENTS

| | | |
|---|---|---|
| 5,531,776 A | 7/1996 | Ward et al. |
| 5,558,665 A | 9/1996 | Kieturakis |

(Continued)

FOREIGN PATENT DOCUMENTS

WO 2012148966 A2 11/2012

OTHER PUBLICATIONS

European Patent Office, Extended Search Report in European Patent Application No. 15754623.5, dated Sep. 29, 2017.
(Continued)

*Primary Examiner* — Carrie R Dorna
(74) *Attorney, Agent, or Firm* — Durham Jones & Pinegar, P.C.

(57) ABSTRACT

A positioning device is configured to selectively position or otherwise manipulate one or more organs within the body of a subject. The positioning device includes a shaped expandable element that is configured to be selectively transitioned between an unexpanded, or collapsed, state and an expanded state. While in the expanded state, the expandable element repositions or otherwise manipulates an organ. Systems that include positioning devices are also disclosed, as are methods for positioning or otherwise manipulating organs.

17 Claims, 4 Drawing Sheets

Related U.S. Application Data

(60) Provisional application No. 61/946,392, filed on Feb. 28, 2014.

(51) Int. Cl.
*A61M 25/00* (2006.01)
*A61B 17/00* (2006.01)
*A61B 17/22* (2006.01)

(52) U.S. Cl.
CPC ............ *A61B 2090/0427* (2016.02); *A61B 2090/3966* (2016.02); *A61M 2025/0096* (2013.01)

(56) References Cited

U.S. PATENT DOCUMENTS

| | | | |
|---|---|---|---|
| 5,716,386 | A | 2/1998 | Ward et al. |
| 6,067,990 | A | 5/2000 | Kieturakis |
| 6,371,910 | B1 | 4/2002 | Zwart et al. |
| 6,632,235 | B2 | 10/2003 | Weikel et al. |
| 6,746,465 | B2 | 6/2004 | Diederich et al. |
| 7,476,235 | B2 | 1/2009 | Diederich et al. |
| 7,621,908 | B2 | 11/2009 | Miller |
| 7,819,817 | B2 | 10/2010 | Rahn |
| 8,273,016 | B2 | 9/2012 | O'Sullivan |
| 8,454,588 | B2 | 6/2013 | Rieker et al. |
| 8,506,589 | B2 | 8/2013 | Maloney |
| 8,529,443 | B2 | 9/2013 | Maloney |
| 9,173,705 | B2 | 11/2015 | Whayne et al. |
| 2003/0114878 | A1 | 6/2003 | Diederich et al. |
| 2004/0147811 | A1 | 7/2004 | Diederich et al. |
| 2007/0066968 | A1 | 3/2007 | Rahn |
| 2007/0118097 | A1 | 5/2007 | Miller |
| 2007/0299433 | A1* | 12/2007 | Williams ............ A61B 18/02 606/21 |
| 2008/0033415 | A1 | 2/2008 | Rieker et al. |
| 2009/0112248 | A1* | 4/2009 | Maloney ............ A61B 18/1492 606/191 |
| 2011/0082488 | A1* | 4/2011 | Niazi ............ A61M 25/1002 606/192 |
| 2011/0282338 | A1 | 11/2011 | Fojtik |
| 2011/0313286 | A1 | 12/2011 | Whayne et al. |
| 2014/0094839 | A1* | 4/2014 | Nimkar ............ A61M 25/0102 606/191 |
| 2015/0196743 | A1 | 7/2015 | Diederich et al. |
| 2015/0245829 | A1 | 9/2015 | Fojtik |
| 2017/0105715 | A1 | 4/2017 | Kasic, II |
| 2018/0035993 | A1 | 2/2018 | Fojtik |

OTHER PUBLICATIONS

Japanese Patent Office, Notice of Reasons for Rejection in Japanese Patent Application No. 2016-554609, dated Oct. 18, 2017.
Japanese Patent Office, Notice of Allowance in Japanese Patent Application No. 2016-554609, dated Aug. 17, 2018.
Japanese Patent Office, Certificate of Patent 6389267 from Japanese Patent Application No. 2016-554609, Aug. 24, 2018.
International Search Report and Written Opinion, International Application No. PCT/US2015/018283, dated May 27, 2015.
USTPO as International Searching Authority, "International Search Report and Written Opinion," International application No. PCT/US2018/047817, dated Dec. 6, 2018.

* cited by examiner

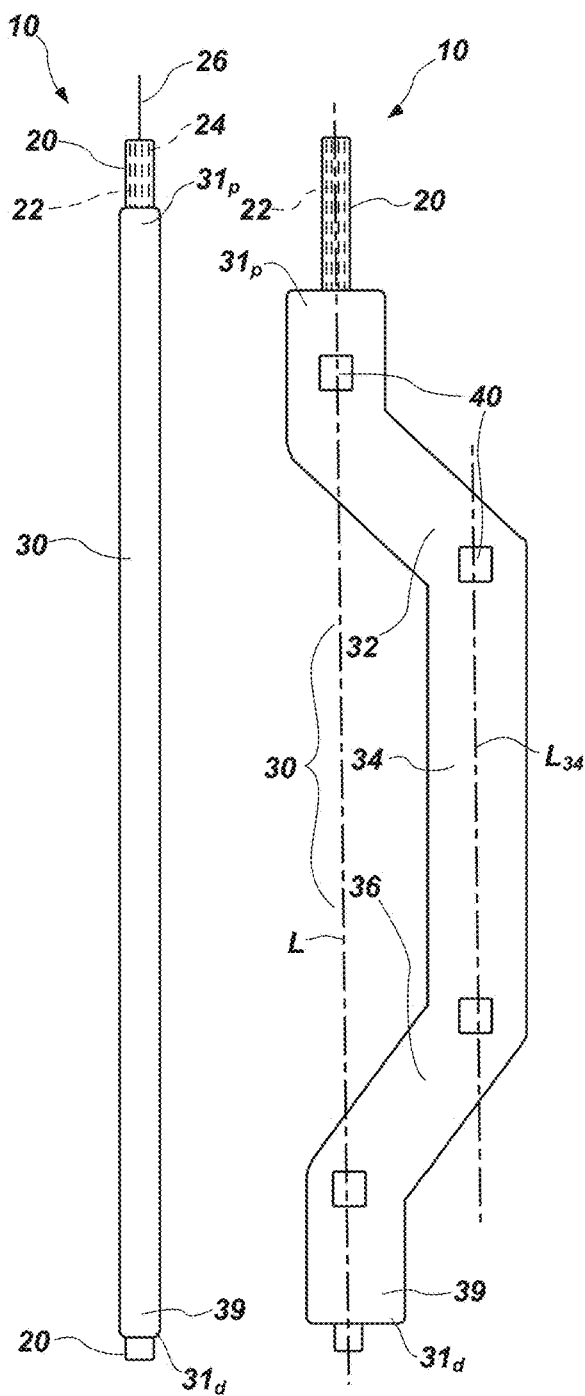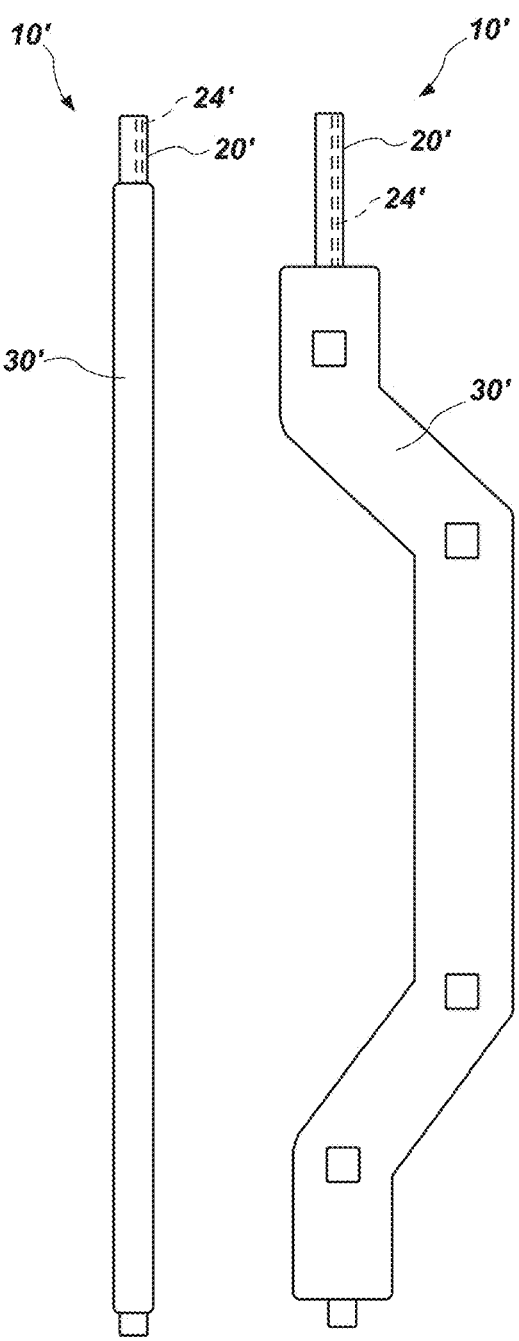
FIG. 1  FIG. 2  FIG. 3  FIG. 4

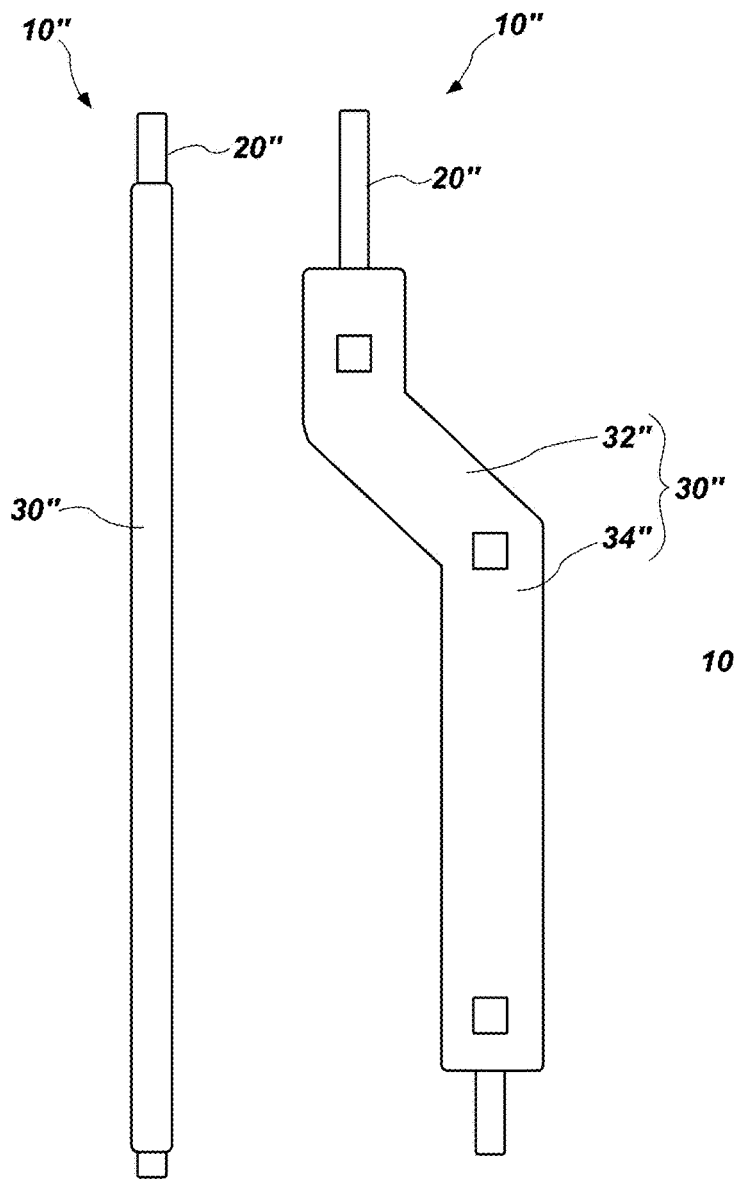
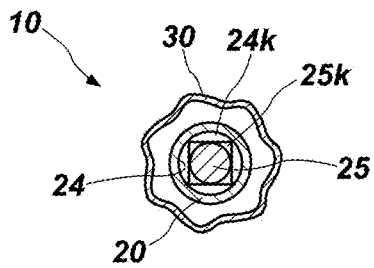
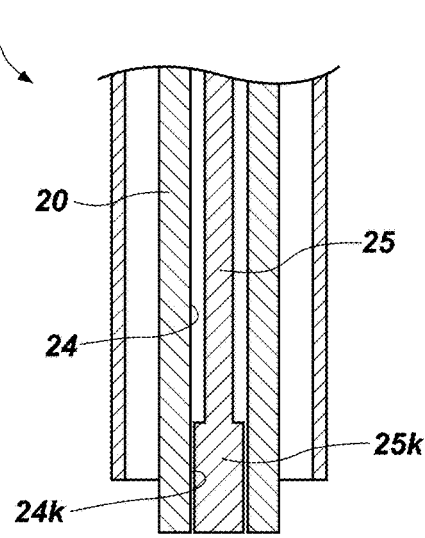
FIG. 5    FIG. 6    FIG. 7    FIG. 8

EXPANDABLE DEVICES FOR POSITIONING ORGANS

CROSS-REFERENCE TO RELATED APPLICATION

This application is a continuation-in-part of U.S. patent application Ser. No. 14/635,435, filed on Mar. 2, 2015 and titled EXPANDABLE DEVICES FOR POSITIONING ORGANS ("the '435 Application"), now U.S. Pat. 10,335,133, issued Jul. 2, 2019. The '435 Application includes a claim for the benefit of priority to the Feb. 28, 2014 filing date of U.S. Provisional Patent Application No. 61/946,392, titled EXPANDABLE DEVICES FOR POSITIONING ORGANS ("the '392 Provisional Application"), pursuant to 35 U.S.C. § 119(e). The entire disclosures of the '392 Provisional Application and the '435 Application are hereby incorporated herein.

TECHNICAL FIELD

This disclosure relates generally to devices for selectively positioning or otherwise manipulating organs (e.g., hollow organs, organs adjacent to internal body cavities, etc.) within the body of a subject. A positioning device according to this disclosure may include an expandable element with a shape that will position a hollow organ, such as an esophagus, in a desired manner. Systems that include organ positioning devices are also disclosed, as are methods for positioning organs.

SUMMARY

A positioning device according to this disclosure may be configured for introduction into a hollow organ or an internal body cavity and against a surface of an organ. The positioning device may include a shaft and an expandable element. The shaft may have a longitudinal axis, which may define the longitudinal axis of the positioning device. The shaft may be configured to enable introduction of the positioning device and, more specifically, its expandable element, into the body of a subject and into a hollow organ that is to be repositioned or otherwise manipulated. Alternatively, the shaft may be introduced into an internal cavity within a subject's body adjacent to at least one organ that is to be repositioned or otherwise manipulated.

The expandable element is positioned along a length of the shaft. It may be located at an intermediate position along a length of the shaft, with portions of the shaft located proximal to and distal to the expandable element. Alternatively, the expandable element may be located along a distal portion of the shaft or extend distally beyond a distal end of the shaft (e.g., the expandable element may be located at a distal end of the shaft, etc.).

The expandable element may have an unexpanded state and an expanded state. The unexpanded state, or collapsed state, of the expandable element may facilitate its introduction into a subject's body and into the hollow organ or internal cavity, as well as its removal from the hollow organ or internal cavity and the body. While in the unexpanded state, the expandable element may be flaccid or substantially flaccid and, thus, easily manipulated (e.g., bent, otherwise conform to a desired shape, etc.).

The expanded state of the expandable element may enable it to assume a desired shape, which may provide the positioning device with an asymmetrical structure. In some embodiments, the expandable element may include a divergent section, a spacing section and, optionally, a convergent section. The divergent section of the expandable element may at least partially diverge from the longitudinal axes of the shaft and the positioning device while in the expanded state. The spacing section of the expandable element, which is distal to the divergent section, may be configured to move, stretch or otherwise manipulate the tissues of a hollow organ in which the expandable element is disposed or an organ against which the expandable element is positioned and, thus, to modify the position and/or shape of the organ. In embodiments where the positioning device includes a convergent section, the convergent section may reinforce the new position and/or shape of a portion of the hollow organ in which the expandable element resides or against which the expandable element has been positioned, as defined at least in part by the spacing section. The various sections of the expandable element may be substantially linear and orientated at angles relative to one another. The corners between the sections of such an angular arrangement may provide structural support that might not be present in embodiments where curved transitions exist between adjacent sections of the expandable element. The abilities of the divergent section, the spacing section, and any optional convergent section to move, reshape, or otherwise manipulate an organ or a portion thereof may, in some embodiments, result from a substantial rigidity (e.g., the rigidity provided by a gas inflated (e.g., to a pressure of about 8 atm. to about 15 atm., etc.) or fluid inflated element, etc.) or a rigidity of the expandable element while in its expanded state.

In some embodiments, the expandable element may be formed from a compliant material (e.g., an elastic material, etc.). In other embodiments, the expandable element may be formed from a less compliant material or from a non-compliant material (e.g., a substantially inelastic material, an inelastic material, etc.), which may be pliable or flexible but substantially inelastic. When the expandable element of a positioning device is formed from a non-compliant material, the extent, or distance, to which the spacing section of the expandable element is moved away from a proximal section of the expandable element and, thus, the extent to which an organ or a portion of an organ may be moved, deflected, or diverted may be determined, at least in part, by an amount of pressure applied to an inflation medium (e.g., a gas, a mixture of gases, air, a liquid, etc.) within the expandable element.

In use, the expandable element of a positioning device, while in its unexpanded state, may be introduced into the body of a subject, and into an interior of a hollow organ or into an internal cavity of the body. In some embodiments, the expandable element may be introduced into the body along a guide wire. Regardless of whether or not a guide wire is used, the shaft of the positioning device may facilitate introduction of the expandable element into the body at a particular location and in a particular orientation within the hollow organ or internal cavity. Once the expandable element is in place within the hollow organ or internal cavity, it may be at least partially expanded. If needed or desired, the position and/or orientation of the expandable element may be adjusted. Positional adjustment may be longitudinal, relative to a length of the positioning device and/or a length of an organ or a cavity within which the expandable element is positioned. Orientational adjustment may be rotational, about the longitudinal axis of the positioning device. Rotational adjustment of the expandable element may be effected by rotating the shaft of the positioning device and/or by rotating a stylet over which the shaft of the positioning device resides. In embodiments where a partially expanded expandable element is moved or its orientation is adjusted, the partially expanded element may be expanded further—even fully expanded. Expansion of the expandable element may move, stretch or otherwise manipulate some or all of the hollow organ or internal cavity. With an organ moved or otherwise manipulated in a desired manner (e.g., to a desired extent, or distance, in a desired direction, etc.), other procedures may be performed. After those procedures are complete, the expandable element may be returned to its unexpanded state, which may reverse movement or other manipulation of part or all of the organ. The expandable element may then be removed from the hollow organ or internal cavity, and the expandable element and the positioning device may be removed from the body of the subject.

Other aspects, as well as features and advantages of various aspects, of the disclosed subject matter will become apparent to those of ordinary skill in the art through consideration of the ensuing description, the accompanying drawings and the appended claims.

BRIEF DESCRIPTION OF THE DRAWINGS

In the drawings:

FIG. 1 illustrates an embodiment of a positioning device, which includes a shaft and an expandable element positioned over an intermediate portion of the shaft, with the expandable element in an unexpanded state;

FIG. 2 illustrates the embodiment of positioning device shown in FIG. 1, with the expandable element in an expanded state;

FIG. 3 depicts another embodiment of positioning device, which includes a shaft and an expandable element positioned over a distal portion of the shaft, with the expandable element in an unexpanded state;

FIG. 4 depicts the embodiment of positioning device shown in FIG. 3, with the expandable element in an expanded state;

FIG. 5 shows yet another embodiment of positioning device, which includes a shaft and another embodiment of expandable element on the shaft, with the expandable element in an unexpanded state;

FIG. 6 shows the embodiment of positioning device depicted by FIG. 5, with the expandable element in an unexpanded state;

FIG. 7 provides a cross-sectional representation through a shaft of a positioning device and through a stylet on which the shaft of the positioning device resides, taken transverse to longitudinal axes of the shaft and the stylet;

FIG. 8 provides a cross-sectional representation of an embodiment of interaction between a shaft of a positioning device and a stylet over which the shaft of the positioning device resides, taken along the longitudinal axes of the shaft and the stylet.

DETAILED DESCRIPTION

Figure 10:
FIGS. 9 through 11 are radiographic images of use of an embodiment of positioning device according to this disclosure in a human esophagus.

With reference to FIGS. 1 and 2, an embodiment of a positioning device 10 that incorporates teachings of this disclosure is illustrated. The positioning device 10, which is configured to move and/or manipulate a portion of a hollow organ within which it is positioned, includes a shaft 20 and an expandable element 30.

The shaft 20 of the positioning device 10 comprises an elongated element, and may include a longitudinal axis L, which may define a longitudinal axis of the positioning device 10. The shaft 20 is configured to enable introduction of the expandable element 30 into the body of a subject, and placement of the expandable element 30 at a desired location and in a desired orientation within the body; for example, within a hollow organ in the body. The shaft 20 may have sufficient flexibility to enable its movement along curved, even tortious, paths through the body of a subject, to enable it to conform to the shape(s) of structures (e.g., organs, etc.) within which or against which it is positioned and/or to enable it to at least partially conform to the shape of the expandable element 30. Flexibility of the shaft 20 may also accommodate changes in the shape of the expandable element 30 as the expandable element 30 expands and/or retracts.

Without limitation, the shaft 20 may comprise a catheter. More specifically, the shaft 20 may comprise an over-the-wire (OTW) catheter, which may be configured to be placed over and introduced into the subject's body along a guide wire. Even more specifically, the shaft 20 may comprise a 6 French (F) to 9 F catheter that is configured for introduction on a 60 PPI to 90 PPI large braid guide wire with an outer diameter of up to about 0.038 inch.

The shaft 20 may be configured to enable remote expansion and retraction of the expandable element 30. In embodiments where the shaft 20 comprises a catheter, the shaft 20 may include a lumen that enables an inflation medium, such as a gas or mixture of gases, air or a liquid, to be introduced into the expandable element 30 and/or withdrawn from the expandable element 30. In other embodiments, the shaft 20 may be configured to accommodate one or more elements (e.g., a control wire, etc.) that enable mechanical expansion and/or retraction of the expandable element 30.

As illustrated by FIGS. 1 and 2, respectively, the expandable element 30 of the positioning device 10 has an unexpanded state and an expanded state. In its unexpanded state, which is depicted by FIG. 1, the expandable element 30 may reside on an outer surface 22 of the shaft 20 without extending substantially beyond the outer surface 22 of the shaft 20. As shown in FIG. 2, in its expanded state, the expandable element 30 may extend beyond the outer surface 22 of the shaft 20. In addition, when the expandable element 30 expands, it may diverge from the longitudinal axes L of the shaft 20 and the positioning device 10.

In the embodiment depicted by FIGS. 1 and 2, the expandable element 30 includes, from its proximal side to its distal side, a divergent section 32, a spacing section 34, and a convergent section 36. The expandable element 30 may also include a distal portion 39. The divergent section 32 may be configured to move a portion of a hollow organ within which the divergent section 32 resides out of its normal location or, in the case of an elongated organ (e.g., an esophagus, a large intestine, a urethra, etc.), out of the normal path of the elongated organ. The spacing section 34, which is distal to the divergent section 32, is configured to hold a portion of an organ within which it resides in a particular position and/or in a particular shape. The convergent section 36, which is adjacent to the distal side of the spacing section 34, may be configured to hold the distal side of the spacing section 34 in place. Optionally, the convergent section 36 may be configured to accommodate organs or other structures within the body of a subject. The distal portion 39, if any, may be aligned with the longitudinal axis L of the shaft 20. In a specific, but non-limiting embodiment, the divergent section 32 of an expandable element 30 having an outer diameter of 14 mm may be capable of offsetting the spacing section 34 up to 7.5 cm from the ends 31$_p$ and 31$_d$ of the expandable element 30 when no external forces (other than ambient external forces, such as the pressure of the atmosphere, gravity, etc.) are exerted on the expandable element 30. Within a subject's esophagus, such a configuration may exert sufficient force on the esophagus to offset a portion of the esophagus by at least 2 cm.

Various transitions, or bends, between differently oriented sections of the expandable element 30 (e.g., the transition between the divergent section 32 and the spacing section 34, the transition between the spacing section 34 and the convergent section 36, the transition between the convergent section 36 and the distal portion 39, etc.) may be smooth. The smoothness of one or more transitions may be configured to reduce or eliminate the likelihood of trauma (i.e., a transition may be atraumatic) during and after placement of the expandable element 30 in its expanded state. In some embodiments, a transition, or bend, may comprise a curve. In other embodiments, a transition, or bend, may include outer corners that are radiused.

In a specific embodiment, in which the positioning device 10 and its expandable element 30 are configured for insertion into and manipulation of a human esophagus, the expandable element 30 may have a length of about 14 cm to about 16 cm, with the spacing section 34, which is located centrally along a length of the expandable element 30, being about 10 cm long. The divergent section 32 and the convergent section 36 may be configured to move the spacing section 34 laterally (in the orientation depicted by FIGS. 1 and 2) to a location that is substantially parallel to the longitudinal axis L, but with a longitudinal axis L34 of the spacing section 34 being offset by about 15 mm from the longitudinal axis L. Upon placing the expandable element 30 in its fully expanded state, its spacing may have any suitable diameter. Without limitation, an outer diameter of the spacing section 34 of the expandable element 30, when fully expanded, may be about 5 mm to about 20 mm (e.g., about 7 mm, about 10 mm, (e.g., for nasal insertion into an esophagus, etc.) about 14 mm (e.g., for oral insertion into an esophagus, etc.), etc.).

The expandable element 30 may, in some embodiments, include one or more radiopaque features 40, which may enable a clinician to determine the position and, optionally, the orientation of the expandable element 30 within a hollow organ of a subject's body. In other embodiments, the expandable element 30 may comprise a radiopaque material (e.g., in embodiments where the expandable element 30 comprises a mesh, etc.).

As suggested previously herein, the expandable element 30 may be configured to be inflated with an inflation medium, such as a gas or mixture of gases, air or a liquid. An expandable element 30 that is configured for inflation may include ends 31$_p$ and 31$_d$ that are sealed against the shaft 20. The shaft 20 of a positioning device 10 with an expandable element 30 may include an inflation/deflation lumen 24 that communicates with an interior of the expandable element 30 and, thus, introduces an inflation medium into the expandable element 30 and removes the inflation medium from the expandable element 30 by way of one or more apertures (not shown) that extend through a wall of the shaft 20, from the inflation/deflation lumen 24 of the shaft 20 to an exterior of the shaft 20.

An expandable element 30 may be shaped in a desired manner, such as that depicted by FIGS. 1 and 2. Cross-sectionally, the expandable element 30 may be circular, elliptical, have a teardrop shape, or have any other shape that will cause little or no trauma during and following expansion of the expandable element 30. The cross-sectional shapes and dimensions of the divergent section 32, the spacing section 34, and the convergent section 36 of the expandable element may be substantially the same, or uniform. Accordingly, the expandable element 30 may be formed from a material that can be shaped as desired. Without limitation, the material of an inflatable expandable element 30 may be moldable, capable of being welded with heat or ultrasonically, or otherwise formed into a desired shape. In addition, the material from which the expandable element 30 is formed may be compliant, semi-compliant, or substantially non-compliant or non-compliant when the expandable element 30 is in its expanded state. Examples of suitable compliant materials for use as at least a portion of the expandable element 30 include, but are not limited to, elastic polyethylenes and polyurethanes. Examples of suitable semi-compliant materials that may be used to form at least a portion of the expandable element 30 include, but are not limited to, some polyethylenes, polyethylene terephthalate, and some vinyl polymers. Examples of substantially non-compliant or non-compliant materials that may be used to form at least a portion of the expandable element 30 include, but are not limited to, some polyethylenes and nylon. When an expandable element 30 that is formed from a substantially non-compliant material or a non-compliant material is fully expanded, it will assume and maintain its predefined shape, whereas the sizes and shapes of expandable elements 30 that are formed from more compliant materials may not be limited to any predefined shape (e.g., they may continue to expand with increased pressure, their shapes may be manipulated even when an inflation medium therein exerts a maximum pressure on them, etc.). Thus, the amount of pressure the inflation medium exerts on such an expandable element 30 may dictate the expanded shape of the expandable element 30 and the distance the spacing section 34 of the expandable element 30 is diverted from the ends 31$_p$ and 31$_d$ of the expandable element 30.

As indicated previously herein, suitable media for expanding inflatable embodiments of expandable elements 30 include gases, gas mixtures, and air. Alternatively, the medium that is used to inflate an inflatable expandable element 30 may comprise a saline solution. In some embodiments, the saline solution may include a radio-opaque material, such as barium or a barium salt.

As an alternative to inflatable expandable elements, an expandable element 30 may be formed from a shaped mesh that surrounds at least a portion of the shaft 20. Without limitation, a shaped mesh may be formed from stainless steel, nitinol, or any other suitable material. The mesh may be formed (e.g., annealed, etc.) to substantially conform to the shape and dimensions of the shaft 20, to enable the expandable element 30 to reside on the shaft 20 when the expandable element 30 is in its unexpanded state. The mesh may also be formed to impart the expandable element 30 with a predetermined shape and dimensions when put in its expanded state.

An expandable element 30 that is formed from or otherwise includes a shaped mesh may be mechanically expanded by any suitable, known means for expansion, such as one or more elements that introduce tension into the shaped mesh to cause it to expand, and that enable the shaped mesh to collapse when the tension is released, or relaxed. As a non-limiting example, an expandable element 30 may include one or more control wires 26 that are configured to mechanically expand and collapse the expandable element 30. Each control wire 26 may comprise a somewhat rigid element that may extend through a lumen 24 of the shaft 20, and may be actuated (i.e., pulled and/or pushed) from a location at or near a proximal end of the shaft 20. As the positioning device 10 is being introduced into the body of a subject, each control wire 26 may be pushed forward to a position that maintains the expandable element 30 in its unexpanded state around and close to the shaft 20. When the expandable element 30 is at an appropriate location within a hollow organ, one or more control wires 26 may be pulled to expand one or more sections of the expandable element 30 a desired extent. Once use of the positioning device 10 is no longer needed (e.g., when deflection or other reshaping of the hollow organ is no longer needed, etc.), each control wire 26 may be pushed, which will cause the expandable element to collapse to its unexpanded state, thereby facilitating removal of the expandable element 30 and the remainder of the positioning device 10 from the hollow organ.

Some embodiments of expandable elements 30 may include individually, or separately, inflatable sections (e.g., divergent section 32, spacing section 34, convergent section 36, etc., may be configured to be inflated and deflated independently from one another). In embodiments where the sections 32, 34, 36 of the expandable element 30 are individually inflatable, each section 32, 34, 36 may communicate with a separate lumen 24 of a catheter that forms at least a part of the shaft 20 and through which inflation and/or deflation of a section 32, 34, 36 of the expandable element 30 may occur. In other embodiments, the sections 32, 34, 36 may be individually expandable and/or retractable by dedicated actuators (e.g., pull wires, etc.).

Expandable elements 30 with separately expandable sections 32, 34, 36 may enable a clinician to selectively expand the expandable element 30 in two or more sequences. As an example, and with continued reference to FIGS. 1 and 2, the spacing section 34 may be expanded first, causing the spacing section 34 to occupy space within the hollow organ. After the spacing section 34 has been at least partially expanded, one or both of the divergent section 32 and the convergent section 36 may be expanded to move the spacing section 34 and the portion of the hollow organ within which the spacing section 34 resides. Such a configuration may provide for increased control over the manner in which a portion of a hollow organ or an entire hollow organ is manipulated, including, without limitation, the distance the hollow organ is diverted or otherwise moved from its original location.

Turning now to FIGS. 3 and 4, an embodiment of a positioning device 10' is illustrated that includes an expandable element 30' that resembles the embodiment of expandable element 30 shown in FIGS. 1 and 2. A shaft 20' of the positioning device 10' is, however, configured to be introduced into a body of a subject, or into a hollow organ within a body of a subject, without the need for a guide wire. The shaft 20' of the positioning device 10' may, therefore, lack a lumen for receiving a guide wire (although it may include one or more lumens 24 for inflating/deflating the expandable element 30 or sections thereof or one or more lumens 24 for accommodating control wires 26 or other elements for expanding and contracting the expandable element 30 or sections thereof).

Referring now to FIGS. 5 and 6, yet another embodiment of positioning device 10" is shown. The positioning device 10" includes a shaft 20" and an embodiment of expandable element 30" that comprises a divergent section 32" and a spacing section 34", but lacks a convergent section 36 (FIGS. 1 and 2).

Turning now to FIGS. 7 and 8, embodiments of features are shown that enable a stylus 25 to rotate a shaft 20 of a positioning device 10 and, thus, to rotationally move an expandable element 30 of the positioning device 10. More specifically a keyed feature $24_k$ within a lumen 24 of the shaft 20 (e.g., a keyed feature $24_k$ that comprises a part of the lumen 24, a keyed feature $24_k$ defined by a structure that has been secured in place within the lumen 24, etc.) may have a configuration that receives and that may be rotationally engaged by a complementarily keyed portion $25_k$ of a stylet 25 over which the shaft 20 resides. The stylet 25 may comprise a permanent feature of the positioning device 10, or it may be capable of assembly with and disassembly from a remainder of the positioning device 10. In the illustrated embodiment, the keyed feature $24_k$ in the lumen 24 and the keyed portion $25_k$ of the stylet 25 have square cross-sectional shapes, as illustrated by FIG. 7. Of course, a variety of other shapes may also be used to enable rotation of the shaft 20 and the expandable element 30 of a positioning device 10 by rotating a stylet 25 over which the positioning device 10 resides. In some embodiments, the keyed feature $24_k$ in the lumen 24 and the keyed portion $25_k$ of the stylet 25 may be located at or near distal ends of the shaft 20 and the stylet 25, respectively. In other embodiments, the keyed feature $24_k$ in the lumen 24 and the keyed portion $25_k$ of the stylet 25 may be located more proximally (e.g., about midway along a height of the expandable element 30, at a location proximal to the expandable element 30, etc.). In any event, when the keyed portion $25_k$ of the stylet 25 is properly positioned within the keyed feature $24_k$ in the lumen 24, rotation, or torquing, of a proximal end of the stylet 25, which may be located outside of a subject's body, may cause the shaft 20 to rotate and, thus, cause rotation of the expandable element 30 about a longitudinal axis of the stylet 25. Such an arrangement may enable rotational positioning of the expandable element 30 to a desired orientation within a hollow organ or a body cavity.

Figure 9:
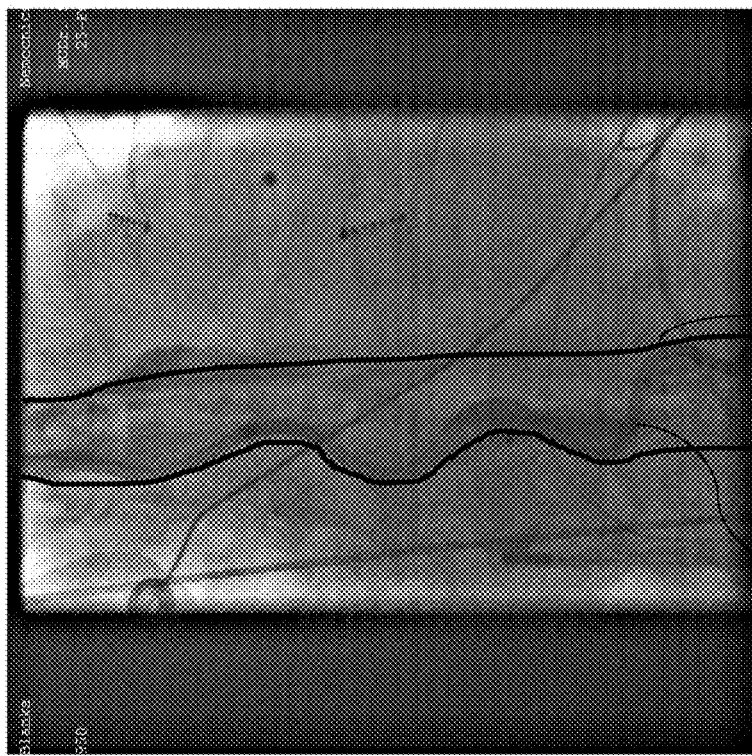
Figure 11:
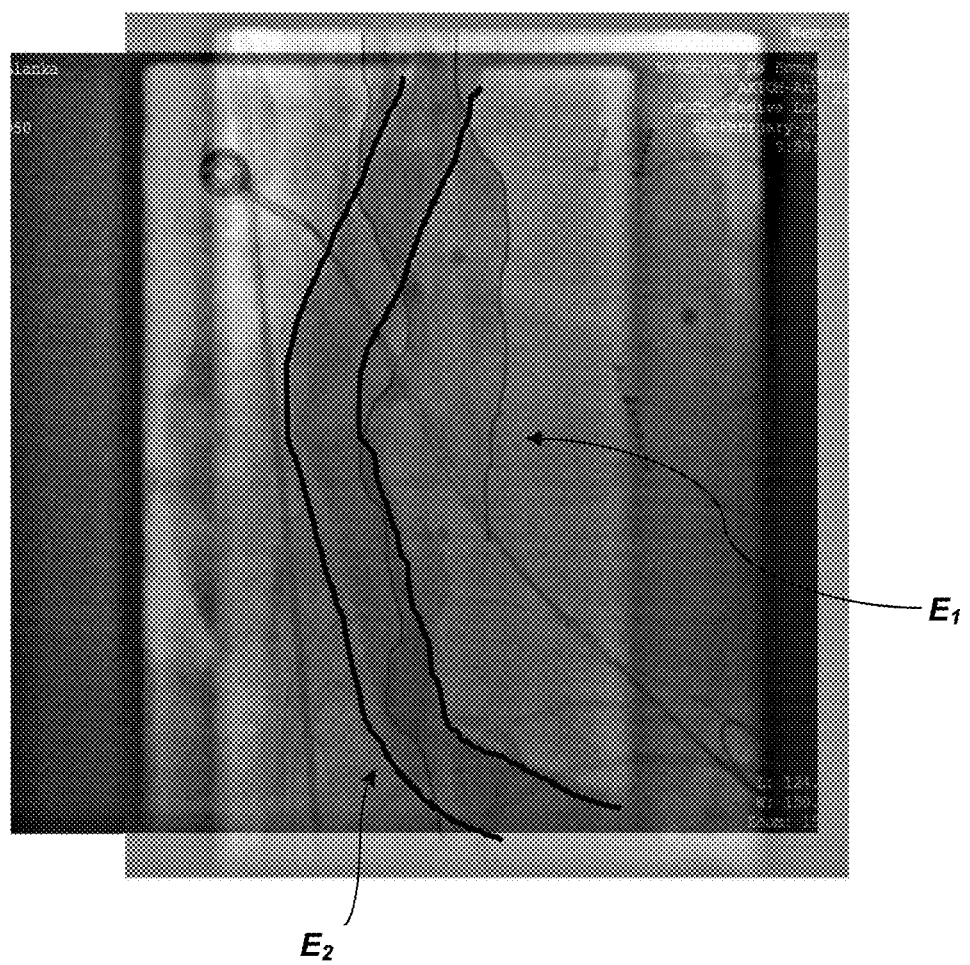

In use, as shown in FIGS. 9 through 11, a positioning device 10 (or any other embodiment of positioning device) according to this disclosure, with its expandable element 30 in an unexpanded state (see, e.g., FIG. 7) may be inserted into a body of a subject and introduced to a desired location and at a desired orientation within the subject's body (e.g., into a hollow organ; into a long organ, such as an esophagus E, a large intestine, a urethra, etc.; into a cavity, such as a nasal cavity; etc.). Without limiting any aspect of this disclosure, insertion of the expandable element 30 into the esophagus E may occur orally or nasally. Once the expandable element 30 is believed to be in the proper position and, optionally, the proper orientation, it may be partially expanded or completely expanded to confirm that its position and, optionally, orientation are proper. The particular location and, optionally, the particular orientation of the expandable element 30 within the subject's body may be determined during or after insertion by any suitable technique (e.g., radiography, etc.). If necessary, the position and/or orientation of the expandable element 30 may be adjusted until it is at a desired location and in a desired orientation. The orientation of the expandable element 30 may be adjusted by rotating the positioning device 10. The expandable element 30 may be at least partially retracted to facilitate such adjustment. Alternatively, an assembly that includes two or more expandable elements 30 with spacing sections 34 that are oriented to be offset in different directions may be used, and the expandable element 30 that is in the desired oriented for moving or offsetting an organ or a portion thereof may be selected from expansion.

With the expandable element 30 at an appropriate location within the subject's body, the expandable element 30 (or the selected expandable element 30) may be partially or fully, or completely, expanded, as shown in FIG. 8, to manipulate the body; for example, the organ within which the expandable element 30 resides or organs that are adjacent to a cavity within which the expandable element resides (e.g., the esophagus E, etc.). The manner in which the expandable element 30 is expanded (e.g., the order in which its sections 32, 34, 36 are expanded, the extent to which the expandable element 30 or one or more of its sections 32, 34, 36 are expanded, etc.) may be controlled. Without limitation, the expandable element 30 may be expanded in a manner that minimizes trauma, in a manner that provides desired movement or reshaping of the organ in which the expandable element 30 resides, etc. In some embodiments, expansion of the expandable element 30 may be visualized (e.g., by radiography, etc.) to confirm that the manner and/or extent of expansion provides one or more desired results (e.g., minimization of trauma, reshaping and/or movement to a desired extent, reshaping and/or movement to a desired extent, etc.). An expandable element 30 and the manner in which it is placed in its expanded state may be configured to move or otherwise manipulate a portion of a long, hollow organ with minimal or no movement of portions of the long, hollow organ that are proximal and distal to the expandable element 30; i.e., without distending the long, hollow organ.

In some embodiments, including embodiments such as that depicted in FIGS. 1 and 2 where the expandable element 30 comprises a balloon with one or more sections formed from a substantially non-compliant material or a non-compliant material, the angles between adjacent ends 31$_p$ and 31$_d$ and sections (e.g., divergent section 32, spacing section 34, convergent section 36, etc.) may decrease as the expandable element 30 is expanded (e.g., inflated, etc.), with each angle approaching 90° as the expandable element 30 is fully expanded. Thus, the pressure an inflation medium exerts on the expandable element 30 may at least partially determine the extent to which the spacing section 34 of the expandable element 30 moves away from the divergent section 32 and the convergent section 36 and, thus, the extent to which the expandable element 30 may deflect a portion of a long, hollow organ. In a specific, but non-limiting, embodiment, an expandable element 30 with a 14 mm outer diameter and a spacing section 34 that is configured to be offset by up to 7.5 cm from ends 31$_p$ and 31$_d$ of the expandable element may be expanded by an inflation medium (e.g., a gas, a mixture of gases, air, etc.) that exerts a pressure of about 4 atm. to about 8 atm. on interior surfaces of the expandable element 30. It may be possible to achieve similar results using less pressure within expandable elements 30 having smaller outer diameters.

FIG. 9 shows the movement achieved between the orientation of expandable element 30 depicted by FIG. 7 (unexpanded) and the orientation of expandable element 30 depicted by FIG. 8 (expanded). In the embodiment illustrated by FIGS. 7 through 9, the esophagus E has been moved about 32 mm away from the left atrium of the heart.

With the expandable element 30 holding the organ in a manipulated state, another procedure may be conducted. As a non-limiting example, an expandable element 30 may deflect an appropriate portion of an esophagus E away from the left atrium of the heart during a left atrial ablation procedure. As another non-limiting example, an expandable element 30 may deflect an appropriate portion of a large intestine or a urethra away from a prostate during biopsy or surgical treatment of a prostate.

Once the surgical procedure is complete or manipulation of the organ is no longer needed, the expandable element 30 may be collapsed around the shaft 20 of the positioning device 10. The expandable element 30 and the remainder of the positioning device 10 may then be removed from the subject's body.

Although the foregoing disclosure provides many specifics, these should not be construed as limiting the scope of any of the ensuing claims. Other embodiments may be devised which do not depart from the scopes of the claims. Features from different embodiments may be employed in combination. The scope of each claim is, therefore, indicated and limited only by its plain language and the full scope of available legal equivalents to its elements.

What is claimed:

1. A positioning device capable of introduction against an interior surface of an organ, comprising:
    a shaft with a longitudinal axis; and
    a balloon at a distal end of the shaft, the balloon including a series of inflatable sections with the series of inflatable sections being oriented at different angles from one another in a manner that enables the balloon to change a path of the organ, with corners having obtuse angles being defined at junctions between adjacent inflatable sections of the series of inflatable sections and inflatable sections of the series of inflatable sections having inflated cross-sectional shapes and dimensions taken transverse to lengths of the inflatable sections that are uniform and substantially the same as one another, the balloon comprising a material that is substantially non-compliant or non-compliant, the balloon being:
    substantially flaccid in an unexpanded state and substantially rigid in an expanded state; and
    asymmetrical about the longitudinal axis in the expanded state such that the positioning device, in the expanded state, is capable of repositioning the organ.

2. The positioning device of claim 1, wherein the balloon, in the expanded state, includes:
    a diverting section that extends away from the longitudinal axis.

3. The positioning device of claim 2, wherein the balloon, in the expanded state, further includes:
    a spacing section distal to the diverting section, at least a portion of the spacing section having a central axis oriented substantially parallel to the longitudinal axis.

4. The positioning device of claim 3, wherein the balloon, in the expanded state, further includes:
    a convergent section distal to the spacing element and extending toward the longitudinal axis.

5. The positioning device of claim 1, wherein the shaft includes a lumen for communicating an inflating medium into a cavity of the balloon to transition the balloon from the unexpanded state to the expanded state.

6. The positioning device of claim 1, further comprising:
    a stylet capable of changing at least one of a position, an orientation, and a configuration of the balloon within the organ.

7. The positioning device of claim 6, further comprising:
    a stylus capable of rotating the positioning device.

8. A positioning device capable of introduction against an interior surface of a hollow organ, comprising:
    a shaft with a longitudinal axis;
    a balloon at a distal end of the shaft, the balloon comprising a material that is substantially non-compliant or non-compliant, the balloon capable of diverting a path of the hollow organ, the balloon including, in series:
a diverting section that extends away from the longitudinal axis;
a spacing section oriented at an angle to and distal to the diverting section, at least a portion of the spacing section being oriented substantially parallel to the longitudinal axis; and
a convergent section oriented at an angle to and distal to the spacing section and extending toward the longitudinal axis,
cross-sectional dimensions of the diverting section, the spacing section and the convergent section, taken transverse to lengths thereof, being uniform and substantially the same as one another, with corners having obtuse angles being defined between the diverting section and the spacing section and between the spacing section and the convergent section upon inflation of the diverting section, the spacing section, and the convergent section.

9. The positioning device of claim 8, wherein the balloon comprises an inflatable balloon having a deflated configuration and an inflated configuration.

10. The positioning device of claim 9, wherein the balloon is flaccid in the deflated configuration and substantially rigid in the inflated configuration.

11. The positioning device of claim 8, further comprising:
a stylet capable of rotating the positioning device.

12. The positioning device of claim 8, wherein the balloon comprises:
a first corner;
the diverting section, including a proximal end continuous with the first corner and a distal end opposite from the proximal end;
a second corner continuous with the distal end of the diverting section;
the spacing section, including a proximal end continuous with the second corner and a distal end opposite from the proximal end;
a third corner continuous with the distal end of the spacing section;
the convergent section, including a proximal end continuous with the third corner and a distal end opposite from the proximal end; and
a fourth corner continuous with the distal end of the convergent section.

13. A method for moving a portion of a hollow organ away from another organ, comprising:
inserting a shaped balloon into the hollow organ, the shaped balloon including a series of expandable sections formed from a non-compliant material;
positioning and orienting the shaped balloon to move the portion of the hollow organ away from another organ;
expanding the shaped balloon, including expanding the series of expandable sections, to increase a rigidity of the shaped balloon, to provide each section of the series of expandable sections with substantially the same uniform cross-sectional shape and dimensions, taken transverse to the length of that section, as the uniform cross-sectional shape and dimensions as each other section of the series of expandable sections and to define corners having obtuse angles between adjacent sections of the series of expandable sections to change a path of the hollow organ to move the portion of the hollow organ away from the another organ.

14. The method of claim 13, further comprising:
conducting a procedure on the another organ with the portion of the hollow organ deflected away from the another organ.

15. The method of claim 13, further comprising:
changing at least one of a position, an orientation, and a configuration of the shaped balloon within the portion of the hollow organ.

16. The method of claim 13, further comprising:
collapsing the shaped balloon; and
removing the shaped balloon from the hollow organ.

17. The method or claim 13, wherein expanding the shaped balloon enables movement of the hollow organ without distension of the hollow organ.

* * * * *